US010136893B2

(12) United States Patent
Farnan

(10) Patent No.: US 10,136,893 B2
(45) Date of Patent: *Nov. 27, 2018

(54) ENDOVASCULAR ANASTOMOTIC CONNECTOR DEVICE, DELIVERY SYSTEM, AND METHODS OF DELIVERY AND USE

(71) Applicant: CircuLite, Inc., Teaneck, NJ (US)

(72) Inventor: Robert C. Farnan, Fort Lauderdale, FL (US)

(73) Assignee: CircuLite, Inc., Teaneck, NJ (US)

( * ) Notice: Subject to any disclaimer, the term of this patent is extended or adjusted under 35 U.S.C. 154(b) by 563 days.

This patent is subject to a terminal disclaimer.

(21) Appl. No.: 14/713,380

(22) Filed: May 15, 2015

(65) Prior Publication Data
US 2015/0245840 A1    Sep. 3, 2015

Related U.S. Application Data

(62) Division of application No. 12/829,425, filed on Jul. 2, 2010, now Pat. No. 9,050,419.
(Continued)

(51) Int. Cl.
*A61B 17/11* (2006.01)
*A61M 1/36* (2006.01)
(Continued)

(52) U.S. Cl.
CPC .............. *A61B 17/11* (2013.01); *A61F 2/954* (2013.01); *A61F 2/958* (2013.01); *A61F 2/962* (2013.01);
(Continued)

(58) Field of Classification Search
CPC .............. A61M 1/3659; A61M 1/3653; A61M 25/0668; A61B 2017/00867; A61B 2017/1107; A61B 2017/1135; A61F 2/064
See application file for complete search history.

(56) References Cited

U.S. PATENT DOCUMENTS 5,474,540 A * 12/1995 Miller ............... A61M 25/0026
604/191
5,486,159 A * 1/1996 Mahurkar ......... A61M 25/0026
604/264
(Continued)

FOREIGN PATENT DOCUMENTS

JP          9511409      11/1997
JP       2005517502 A    6/2005
(Continued)

OTHER PUBLICATIONS

Japanese Patent Office, Notice of Reasons for Rejection in JP Application No. 2014-206184, dated Aug. 31, 2015.
(Continued)

*Primary Examiner* — Dianne Dornbusch
(74) *Attorney, Agent, or Firm* — Christopher & Weisberg, P.A.

(57) ABSTRACT

An endovascular anastomotic connector and method of using the same. The endovascular anastomotic connector includes a vascular conduit and a supply conduit. The vascular conduit has proximal and distal ends that reside within a vascular structure. The supply conduit extends at an angle from the vascular conduit. The proximal end of the supply conduit is configured to be attached to an auxiliary device.

7 Claims, 11 Drawing Sheets

Related U.S. Application Data

(60) Provisional application No. 61/242,153, filed on Sep. 14, 2009.

(51) Int. Cl.
| | | |
|---|---|---|
| *A61F 2/954* | (2013.01) | |
| *A61F 2/958* | (2013.01) | |
| *A61F 2/962* | (2013.01) | |
| A61B 17/00 | (2006.01) | |
| A61F 2/06 | (2013.01) | |
| A61M 25/06 | (2006.01) | |

(52) U.S. Cl.
CPC ........ *A61M 1/3653* (2013.01); *A61M 1/3659* (2014.02); *A61B 2017/00778* (2013.01); *A61B 2017/00867* (2013.01); *A61B 2017/1107* (2013.01); *A61B 2017/1135* (2013.01); *A61F 2/064* (2013.01); *A61M 25/0668* (2013.01)

(56) References Cited

U.S. PATENT DOCUMENTS

| | | | | |
|---|---|---|---|---|
| 5,613,980 A | * | 3/1997 | Chauhan | A61M 25/1002 128/898 |
| 5,669,924 A | * | 9/1997 | Shaknovich | A61F 2/07 604/101.04 |
| 5,720,735 A | * | 2/1998 | Dorros | A61F 2/90 604/284 |
| 5,807,311 A | * | 9/1998 | Palestrant | A61M 25/003 604/28 |
| 6,017,363 A | * | 1/2000 | Hojeibane | A61F 2/856 606/194 |
| 6,099,497 A | * | 8/2000 | Adams | A61F 2/856 604/101.01 |
| 6,129,738 A | * | 10/2000 | Lashinski | A61F 2/954 604/101.04 |
| 6,162,196 A | * | 12/2000 | Hart | A61B 17/3462 604/167.02 |
| 6,183,509 B1 | * | 2/2001 | Dibie | A61F 2/91 623/1.16 |
| 6,361,544 B1 | * | 3/2002 | Wilson | A61F 2/856 604/101.01 |
| 6,482,211 B1 | * | 11/2002 | Choi | A61F 2/954 604/103.03 |
| 6,592,544 B1 | * | 7/2003 | Mooney | A61M 39/0693 604/35 |
| 6,719,749 B1 | * | 4/2004 | Schweikert | A61M 25/0009 604/28 |
| 7,014,628 B2 | * | 3/2006 | Bousquet | A61M 1/285 128/DIG. 26 |
| 2002/0052648 A1 | | 5/2002 | McGuckin et al. | |
| 2004/0167478 A1 | * | 8/2004 | Mooney | A61B 17/3417 604/264 |
| 2004/0168691 A1 | | 9/2004 | Sharkawy et al. | |
| 2004/0243095 A1 | * | 12/2004 | Nimkar | A61M 25/0102 604/500 |
| 2005/0096585 A1 | * | 5/2005 | Schon | A61M 25/0026 604/43 |

FOREIGN PATENT DOCUMENTS

| | | |
|---|---|---|
| JP | 2008511419 A | 4/2008 |
| JP | 2008513155 A | 5/2008 |
| JP | 2009525128 A | 7/2009 |
| WO | 9514442 A1 | 6/1995 |
| WO | 2006028925 A1 | 3/2006 |
| WO | 2007089500 A2 | 8/2007 |
| WO | 2008027869 A2 | 3/2008 |
| WO | 2009082718 A1 | 7/2009 |

OTHER PUBLICATIONS

Japanese Patent Office, Decision of Rejection in JP Application No. 2014-206184, dated May 9, 2016.

Canadian Intellectual Property Office, Office Action in Canadian Application No. 2,768,567, dated Jan. 26, 2016.

* cited by examiner

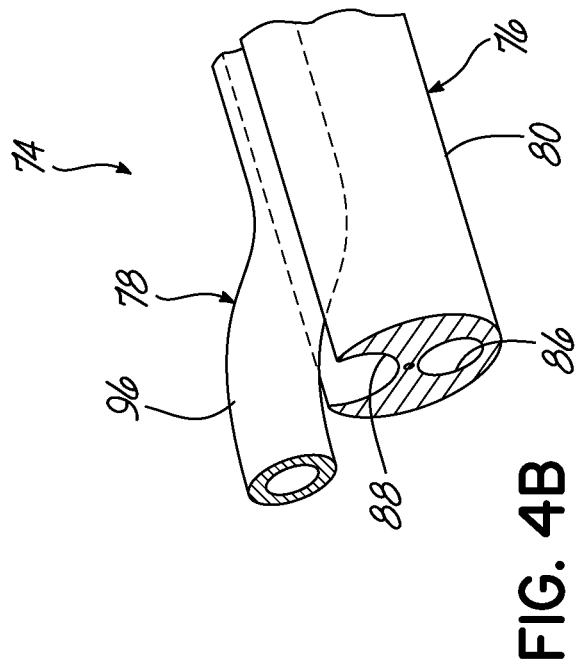
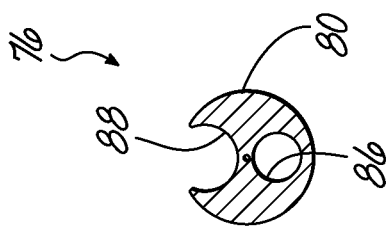
FIG. 4B
FIG. 4A

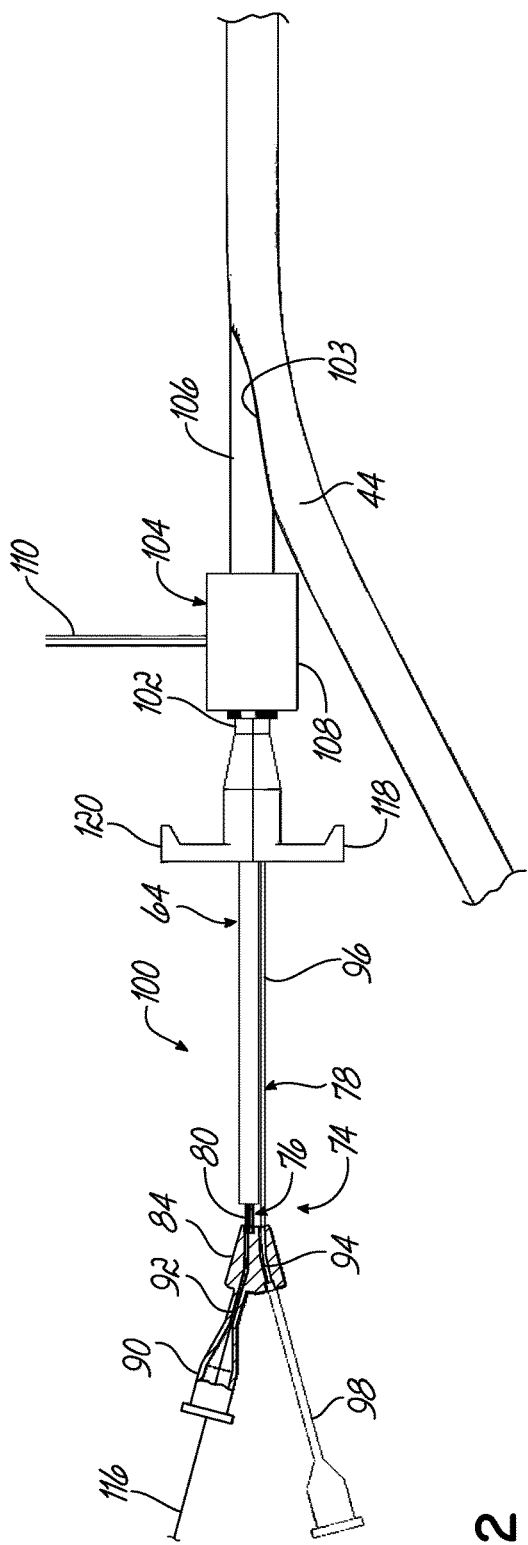
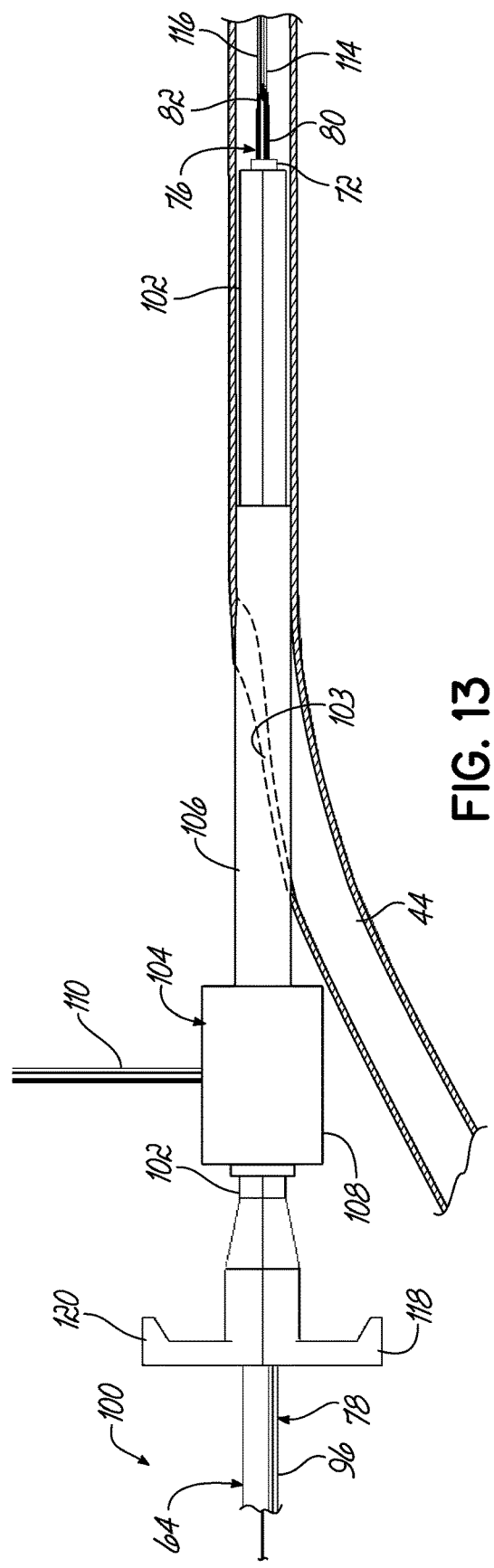

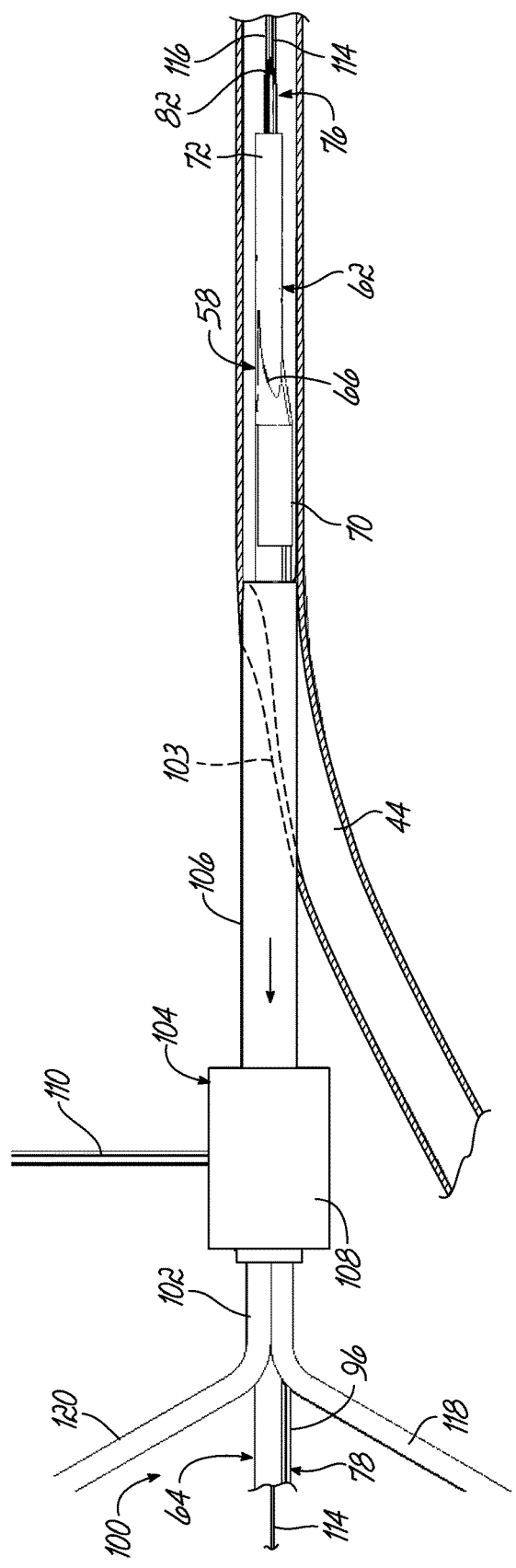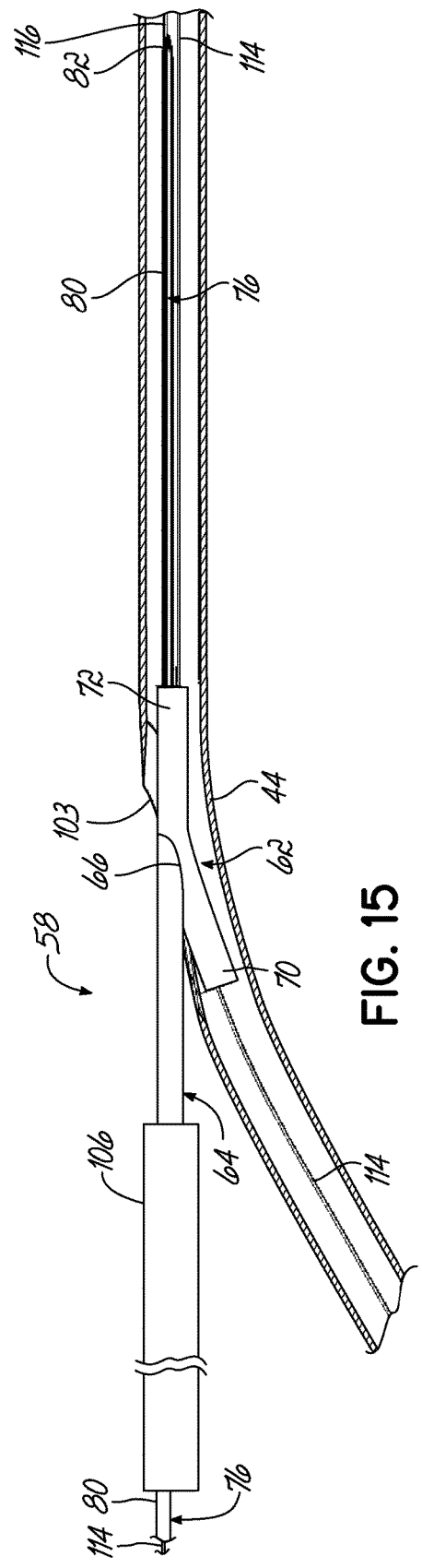
FIG. 14
FIG. 15

ENDOVASCULAR ANASTOMOTIC CONNECTOR DEVICE, DELIVERY SYSTEM, AND METHODS OF DELIVERY AND USE

CROSS-REFERENCE TO RELATED APPLICATION

This application is a divisional of application Ser. No. 12/829,425 filed Jul. 2, 2010, which is now U.S. Pat. No. 9,050,419, which claims the priority of U.S. Provisional Patent Application Ser. No. 61/242,153, filed on Sep. 14, 2009, the disclosure of which are hereby incorporated by reference herein.

TECHNICAL FIELD

The present invention relates generally to vascular connector devices and methods of using the same. More specifically, the invention relates to an endovascular anastomotic connector, a delivery system, and a method of delivery.

BACKGROUND

The circulatory system of the human body transports blood containing chemicals, such as metabolites and hormones, and cellular waste products to and from the cells. This organ system includes the heart, blood, and a vascular network. Veins are vessels that carry blood toward the heart while arteries carry blood away from the heart. The human heart consists of two atrial chambers and two ventricular chambers. Atrial chambers receive blood from the veins and the ventricular chambers, which include larger muscular walls, pump blood from the heart. Movement of the blood is as follows: blood enters the right atrium from either the superior or the inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and flows into the left ventricle. Finally, the blood is pumped from the left ventricle into the aorta and the vascular network.

In some instances, it becomes necessary to maintain fluidic communication with the vascular network. For example, a circulatory assist system uses a pump to aid in moving blood through the vascular network, thereby relieving the symptoms associated with congestive heart failure (commonly referred to as heart disease). The pump of the circulatory assist system includes inflow and outflow cannulae. Often the inflow cannula connects the left atrium of the heart to the pump; the outflow cannula connects the pump to a peripheral artery. The outflow cannula must be stabilized within the peripheral artery to ensure proper functioning of the circulatory assist system and reduce the risk of bleeding. Accordingly, it would be beneficial to have devices that can be delivered and secured to a peripheral vessel but are also capable of being attached to an auxiliary device.

SUMMARY

In one illustrative embodiment of the present invention, an anastomotic connector is described. The anastomotic connector includes a vascular conduit and a supply conduit. The vascular conduit has proximal and distal ends that reside within a vascular structure. The supply conduit extends at an angle from the vascular conduit. The proximal end of the supply conduit is configured to extend from the vascular structure and attach to an auxiliary device.

In another illustrative embodiment of the present invention, a delivery system is described and includes the anastomotic connector and a delivery subassembly. The delivery subassembly includes a multi-lumen hub, a multi-lumen delivery shaft, and a secondary delivery shaft. The multi-lumen delivery shaft extends from the multi-lumen hub, through the lumen of the supply conduit, and out from the distal end of the vascular conduit. The secondary delivery shaft extends from the multi-lumen hub, into the proximal end of the vascular conduit, and out from the distal end of the vascular conduit. A proximal portion of the secondary delivery shaft extending from the distal end of the vascular conduit is received by a first lumen of the multi-lumen delivery shaft.

BRIEF DESCRIPTION OF THE FIGURES

FIG. 4A is a cross-sectional view of the multi-lumen delivery shaft taken along the line 4A-4A of FIG. 3.

FIG. 4B is an isometric view of the multi-lumen delivery shaft with the secondary delivery shaft taken from the enclosure 4B of FIG. 2.

FIGS. 8 and 9 are side-elevational views illustrating successive steps of one exemplary procedure for loading the delivery assembly into a delivery sheath.

FIGS. 10-16 are side-elevational views, in partial cross section, illustrating successive steps of one exemplary procedure for inserting and deploying the endovascular anastomotic connector in a peripheral artery.

DETAILED DESCRIPTION

Figure 1:
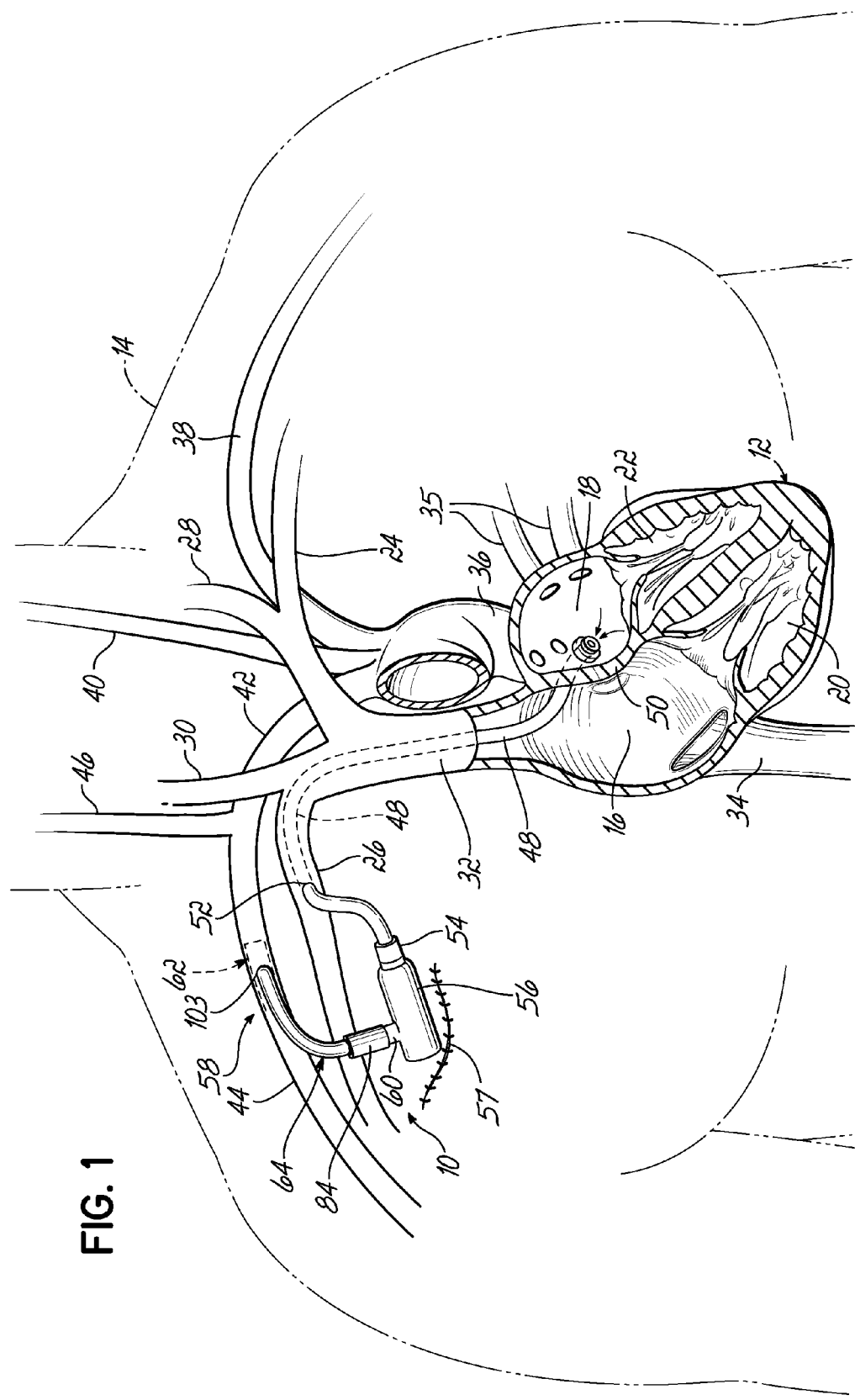
FIG. 1 is a diagrammatic view of a circulatory assist system with the outflow of the pump being connected to a peripheral artery with an endovascular anastomotic connector, shown in partial cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 35 and is then pumped into the left ventricle 22. Blood leaving the left ventricle 22 enters the aortic arch 36 and flows into the left subclavian artery 38, the left common carotid 40, and the brachiocephalic trunk 42 including the right subclavian artery 44 and the right common carotid 46.

With respect to the implanted circulatory assist system 10, a flexible cannula body 48 extends from within the left atrium 18, through the intra-atrial septum 50, and percutaneously to a vascular access site 52 in the right subclavian vein 26. The flexible cannula body 48 is attached to an input port 54 of an implantable pump 56. An endovascular anastomotic connector 58 connects an output port 60 of the implantable pump 56 to a suitable superficial artery, such as the right subclavian artery 44. The physician can position the implantable pump 56 subcutaneously and, optionally, submuscularly in a pump pocket 57 located near the vascular access site 52 or maintain the pump 56 externally.

Figure 1A:
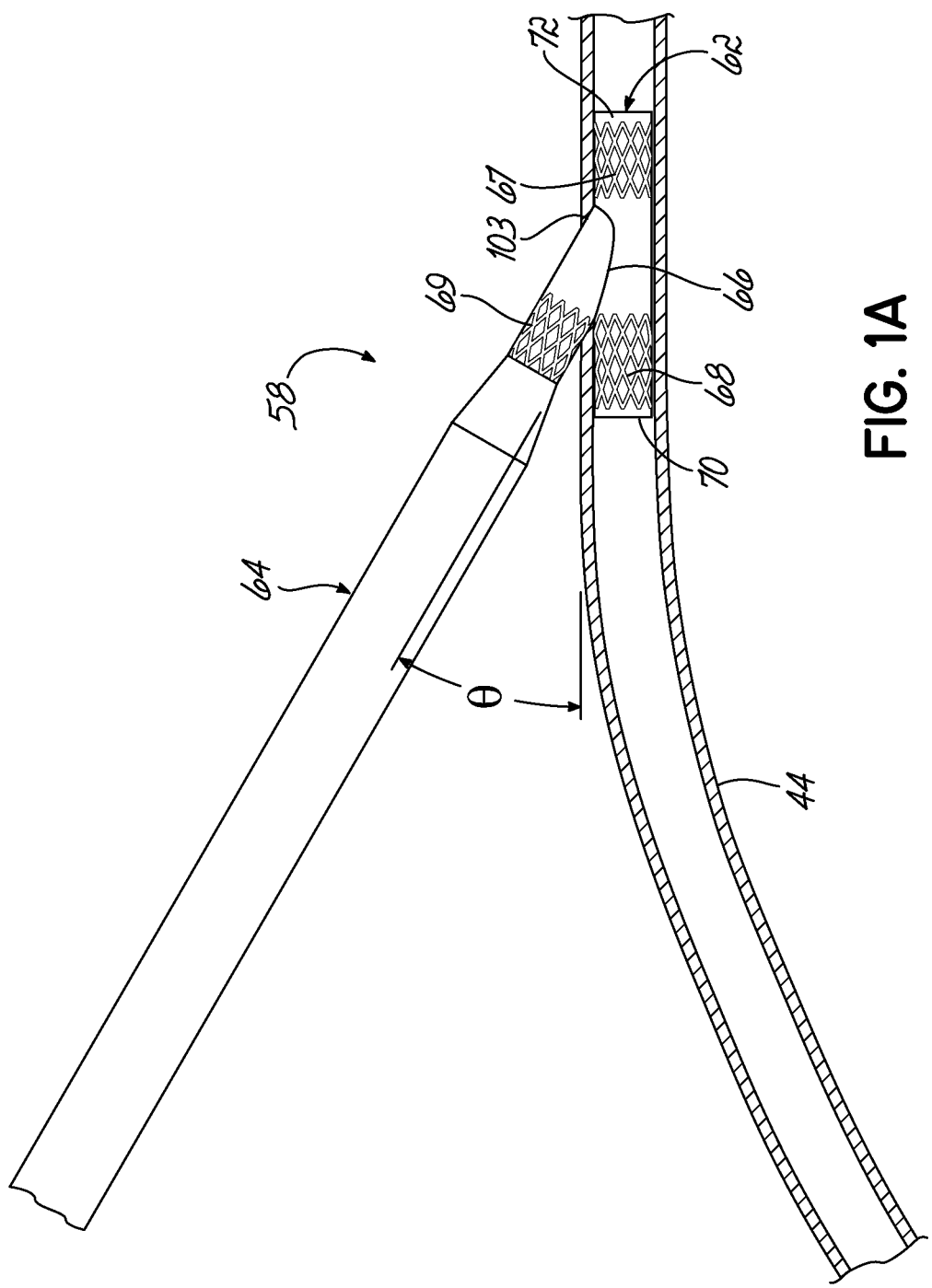
FIG. 1A is a side-elevational view, in partial cross section, of the endovascular anastomotic connector in a peripheral artery.

The endovascular anastomotic connector 58 is shown in greater detail in FIG. 1A. For illustrative purposes, the endovascular anastomotic connector 58 is shown to be implanted within the right subclavian artery 44; however, any suitable peripheral vessel could be used. The endovascular anastomotic connector 58 includes a vascular conduit 62 and a supply conduit 64 that extends angularly from the vascular conduit 62. The junction between the vascular and supply conduits 62, 64 forms a bifurcation joint 66. In some embodiments, the vascular conduit 62 can be a vascular stent.

The vascular and supply conduits 62, 64 can each include support structures 67, 68, 69 constructed from continuous wire or laser cut from a hypotube or rolled sheet stock. The support structures 67, 68, 69 are then encapsulated within an expandable material. The expandable material can be superelastic and self-expanding, such as nickel titanium (NiTi). Alternatively, a balloon-expandable material, such as nickel cobalt (NiCo) or chromium cobalt (CrCo) can be used. The expandable material can then be coated with a porous material to allow for the migration of endothelial cells, and to secure the conduits 62, 64 to the wall of the vessel. Suitable porous materials can include expanded polytetrafluoroethylene (ePTFE), woven polyester, velour, or DACRON brand of synthetic polyester fabric. In some embodiments, the wall thickness of the vascular conduit 62 can be thinner than the wall thickness of the supply conduit 64 to allow the vascular conduit 62 to conform to the lumen of the blood vessel while not obstructing the flow of blood through the vessel. This is more preferred over the reverse because the vascular conduit 62 is implanted within the vessel and the profile should be minimized so as to not interfere with blood flow.

The bifurcated joint 66 should be flexible and replicate the vessel's native compliance. The bifurcated joint 66 can form an angle, θ, which can vary from about 5° to about 90° (i.e., perpendicular) depending on the intended use of the endovascular anastomotic connector 58 and the local anatomy.

Figure 2:
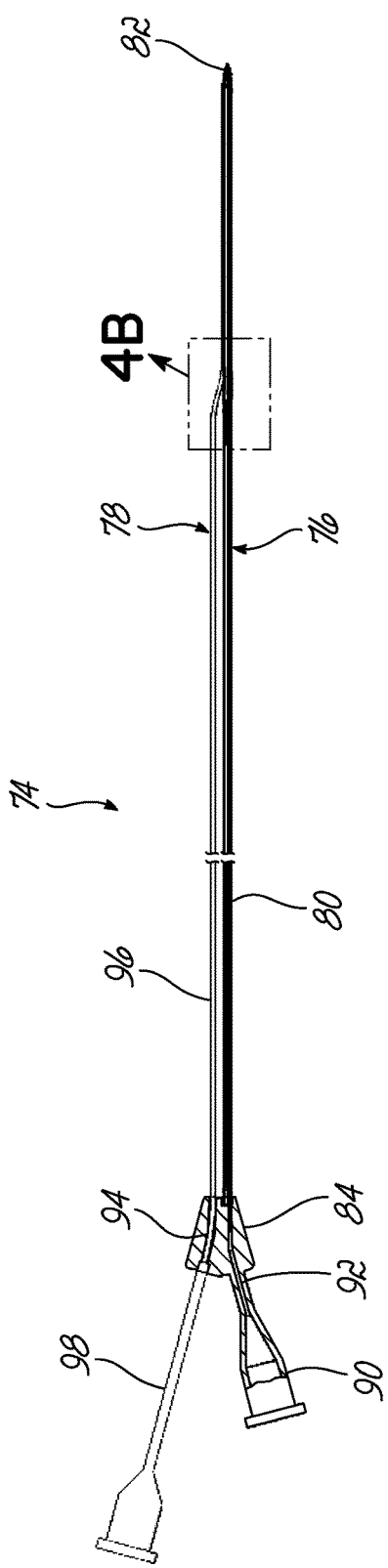
FIG. 2 is a side-elevational view, in partial cross section, of a delivery subassembly for advancing and deploying the endovascular anastomotic connector.

Turning now to FIG. 2, a delivery subassembly 74 for delivering the endovascular anastomotic connector 58 (FIG. 1A) is shown. The delivery subassembly 74 includes a multi-lumen delivery shaft 76 and a secondary delivery shaft 78.

Figure 3:
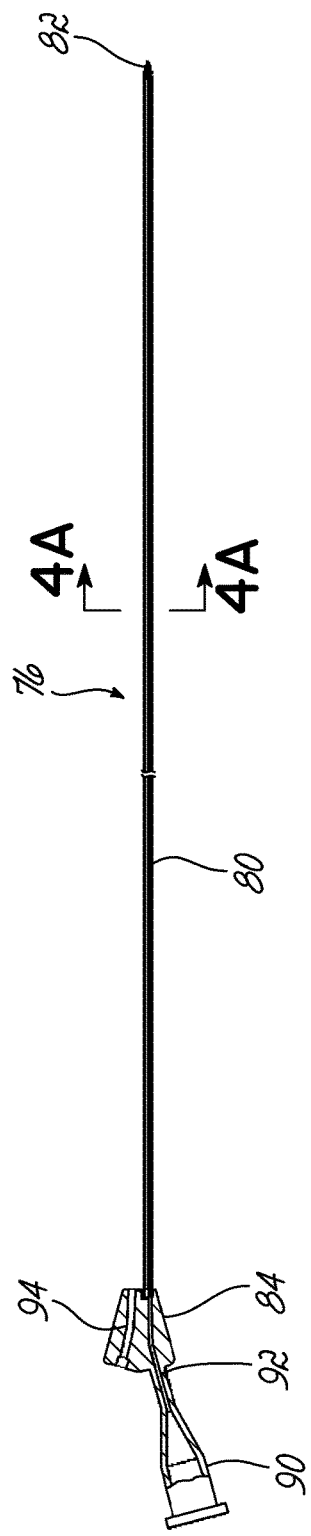
FIG. 3 is a side-elevational view, in partial cross section, of a multi-lumen delivery shaft of the delivery subassembly.

The multi-lumen delivery shaft 76, illustrated alone in FIG. 3, includes a multi-lumen tube 80 having a formed tip 82 and a multi-lumen hub 84. The cross-section of one suitable multi-lumen tube 80 is shown in FIG. 4A and includes primary and secondary lumens 86, 88, both of which extend from the distal formed tip 82 to the multi-lumen hub 84. The primary lumen 86 is sized to receive a conventional guide-wire. The secondary lumen 88 is sized to receive the secondary delivery shaft 78 and can be slotted to aid in assembly as will be described below. The multi-lumen tube 80 can be constructed by an extrusion process from a thermoplastic material. The formed tip 82 minimizes trauma to vascular tissues as the delivery subassembly 74 is advanced through the vascular network.

FIG. 4B is an enlarged view of one manner by which the secondary lumen 88 of the multi-lumen delivery shaft 76 receives a portion of the secondary delivery shaft 78, as illustrated in FIG. 2.

Figure 5:
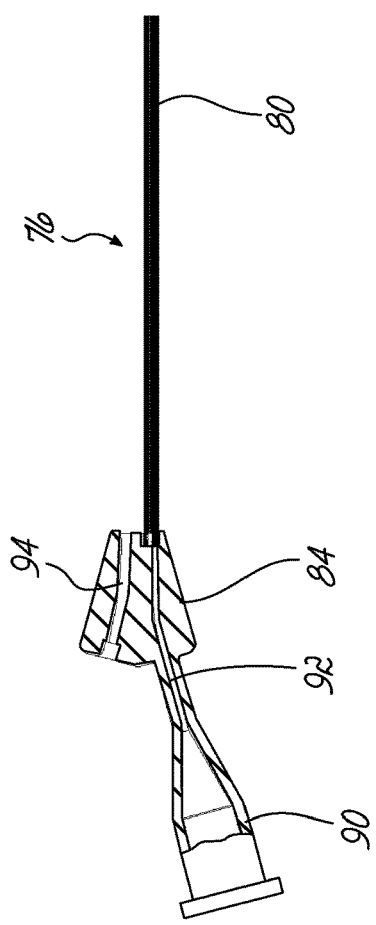
FIG. 5 is a partial side-elevational view, in partial cross section, of the multi-lumen hub and a luer adapter of the delivery subassembly.

FIG. 5 illustrates, in greater detail, the multi-lumen hub 84. The multi-lumen hub 84 can be molded directly onto the proximal end of the multi-lumen tube 80 or molded separately and then affixed to the multi-lumen tube 80 with an epoxy or a biocompatible adhesive, such as UV or cyanoacrylate. A luer adaptor 90 is connected to a first lumen 92 for flushing the primary lumen 86 (FIG. 4) of the multi-lumen tube 80 prior to implantation. A second lumen 94 of the multi-lumen hub 84 is sized to receive the secondary delivery shaft 78.

Figure 6:
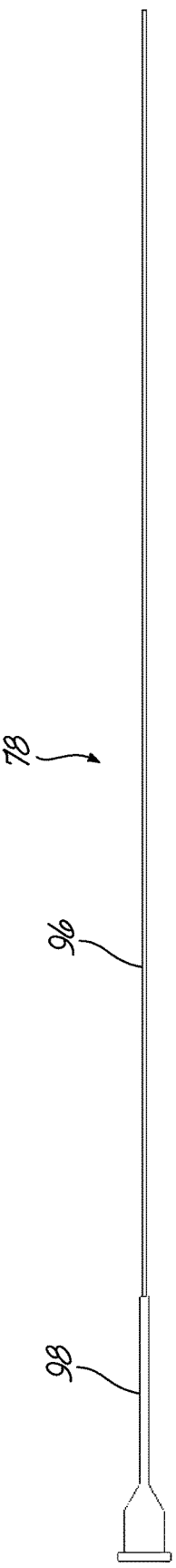
FIG. 6 is a side-elevational view of the secondary delivery shaft of the delivery subassembly.

FIG. 6 illustrates the secondary delivery shaft 78, which can include a single lumen tube 96 and a proximal hub luer 98. The single lumen tube 96 can be constructed using an extrusion process and can be sized to receive a conventional guide-wire. The hub luer 98 can be separately constructed and attached to the single lumen tube 96 with a biocompatible adhesive or epoxy. The hub luer 98 allows flushing of the secondary delivery shaft 78 prior to insertion.

Figure 7C:
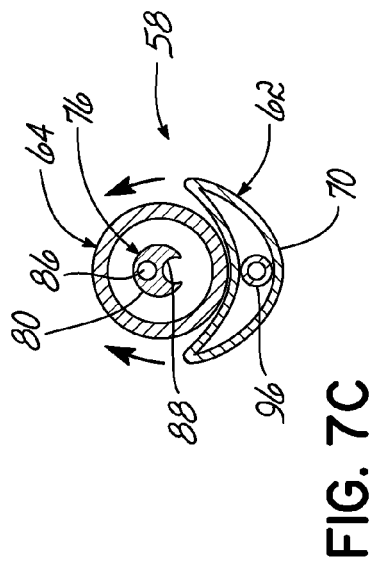
FIG. 7C is a cross-sectional view of one exemplary method of folding the endovascular anastomotic connector around the delivery subassembly, taken along the line 7C-7C of FIG. 7B.
Figure 7A:
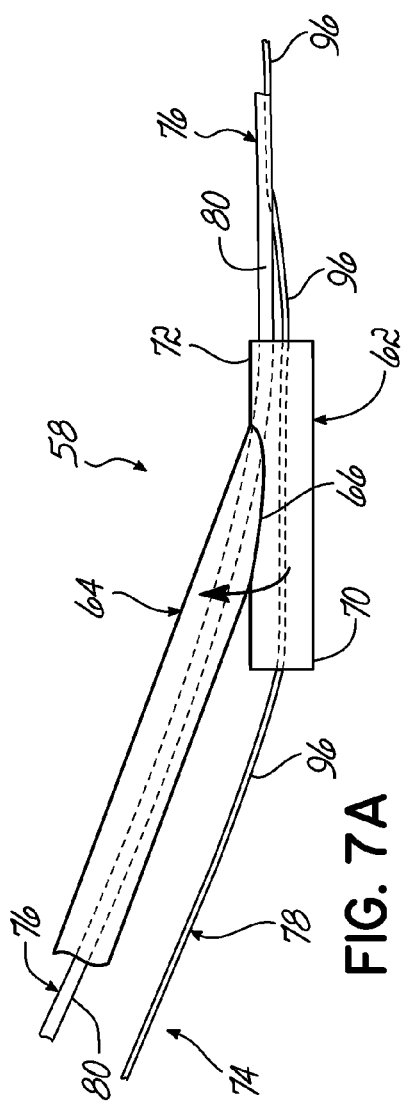
FIG. 7A is a side-elevational view of one exemplary method of loading the endovascular anastomotic connector onto the delivery subassembly.
Figure 7B:
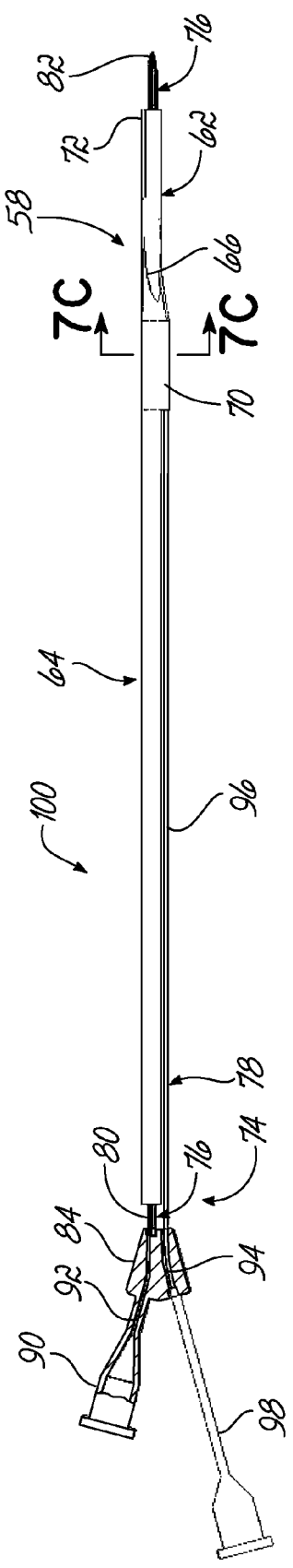
FIG. 7B is a side-elevational view, in partial cross section, of the delivery assembly.
Figure 10:
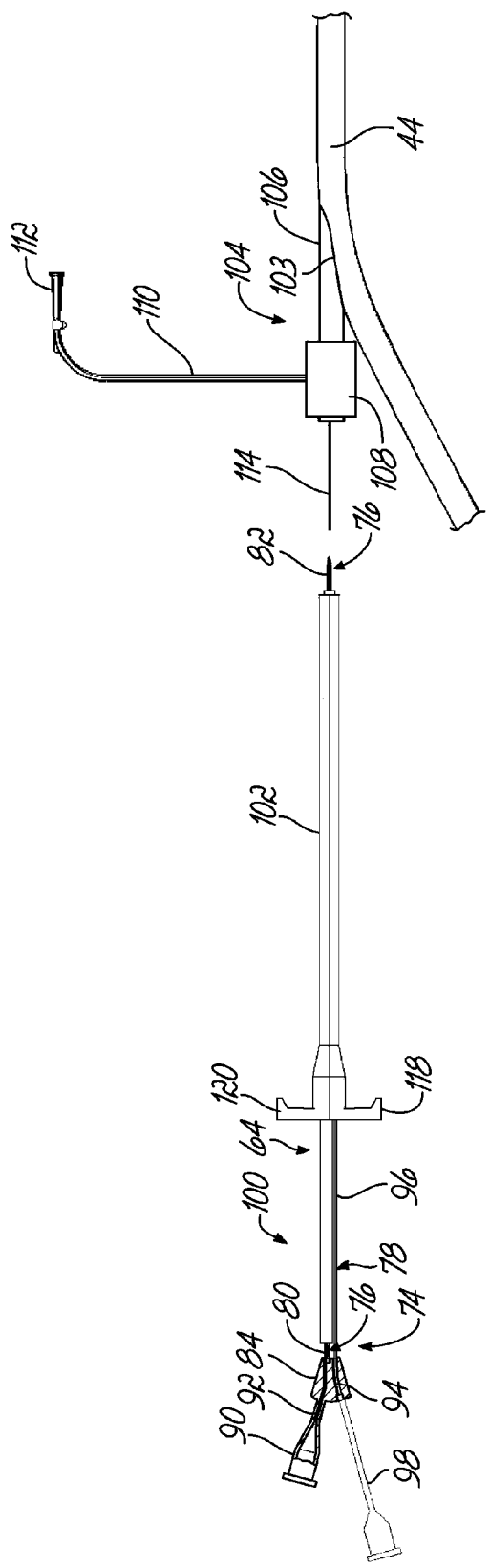

FIGS. 7A-7C illustrate one method of loading the endovascular anastomotic connector 58 onto the delivery subassembly 74. It should be noted that the delivery subassembly 74 has been rotated 180° about a longitudinal, lengthwise axis for illustrating the loading and delivery of the endovascular anastomotic connector 58.

In FIG. 7A the multi-lumen delivery shaft 76 is directed into the proximal end of the supply conduit 64. The formed tip 82 is advanced through the supply conduit 64 until it exits from the distal end 72 of the vascular conduit 62. The secondary delivery shaft 78 is advanced through the second lumen 94 of the multi-lumen hub 84, along the outside of the supply conduit 64, and into the proximal end 70 of the vascular conduit 62. The distal end of the secondary delivery shaft 78 is then advanced beyond the distal end 72 of the vascular conduit 62 and clipped into the slotted secondary lumen 88 of the multi-lumen tube 80. The assembled delivery system 100 is shown in FIG. 7B.

The endovascular anastomotic connector 58 can be folded about the delivery subassembly 74 to minimize the delivery system profile. One manner of folding the endovascular anastomotic connector 58 includes collapsing the support structures 67, 69 (FIG. 1A) of the distal end 72 of the vascular conduit 62 and the supply conduit 67, respectively and wrapping the distal end 72 and the supply conduit 67 around the multi-lumen delivery shaft 76. Then, after the secondary delivery shaft 78 is inserted through the proximal end 70 of the vascular conduit 62, the support structure 68 is collapsed and the proximal end 70 is wrapped around the supply conduit 64 in a "c" shape, as shown in FIG. 7C. In this way, the vascular conduit 62 can be deployed and positioned within the vessel before the supply conduit 64 seals the incision in the wall of the vessel.

Figures 8, 9:
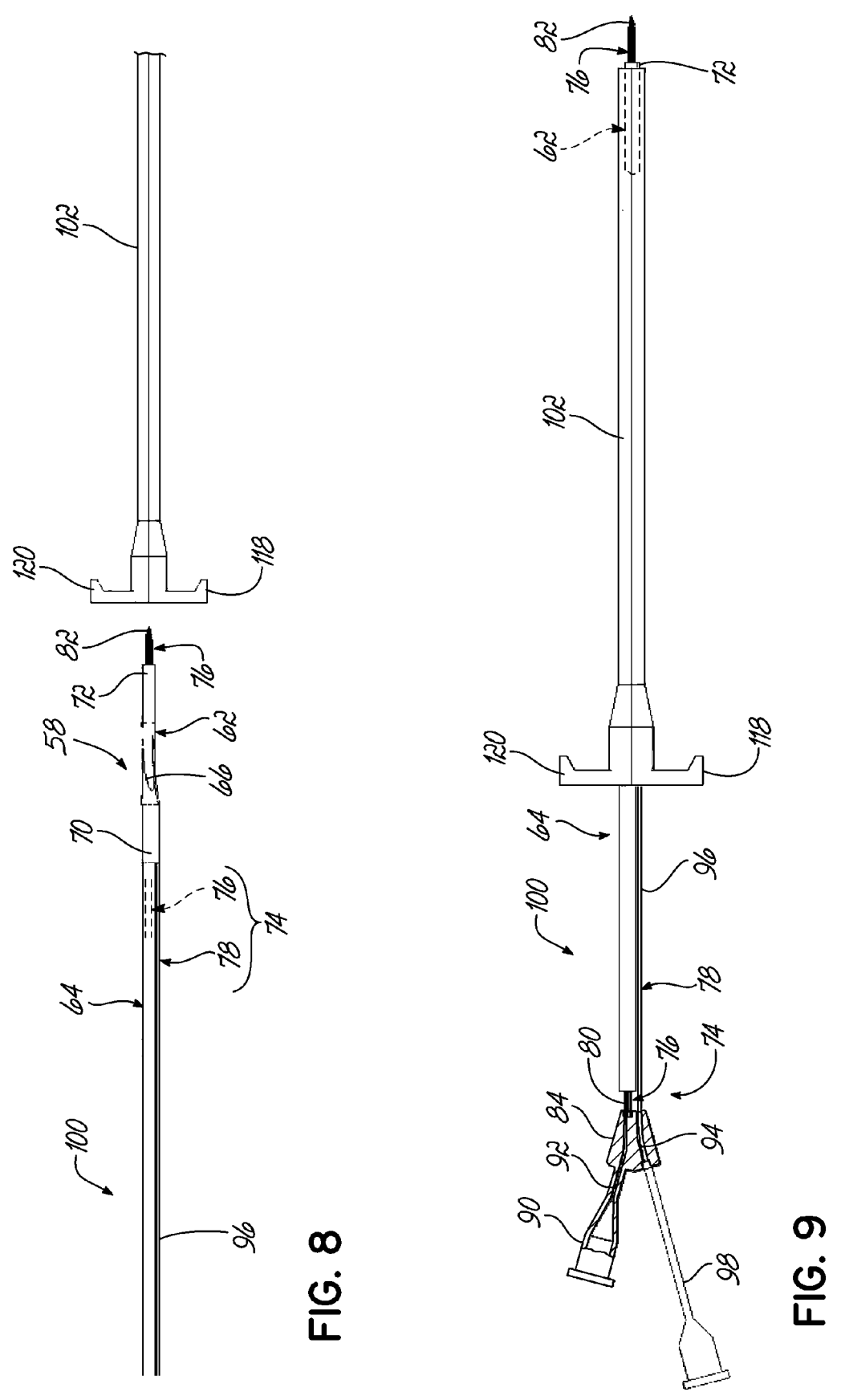

After assembly, the delivery system 100 is back-loaded into a delivery sheath 102, as shown in FIG. 8. The delivery sheath 102 can be constructed from a peel-away sheath design for ease of removal. FIG. 9 illustrates the delivery system 100 loaded within the delivery sheath 102.

One manner of inserting the endovascular anastomotic connector 58 into a vessel can now be described with reference to FIGS. 10-16. The method begins with the physician creating an incision 103 into a suitable peripheral vessel, illustrated here as the right subclavian artery 44. The selection of the peripheral vessel is dependent on the particular surgical procedure. For example, in the implantation of the circulatory assist system 10 (FIG. 1), the right subclavian artery 44 can be appropriate when the pump pocket 57 (FIG. 1) is located near the right subclavian vein 26. An introducer 104 can be directed into the right subclavian artery 44 to maintain the incision 103 into the vessel. A suitable introducer 104 could include those that are commercially available or a custom introducer, such as the one disclosed in U.S. Provisional Patent Application No. 61/163,931, filed on Mar. 27, 2009, the disclosure of which is incorporated herein by reference. The illustrated introducer 104 includes a sheath 106 with a proximal hub 108. The hub includes a side port 110 and a valve 112 for fluidic access.

The physician can then create a secondary incision site (not shown) that is remotely located from the incision 103 in the right subclavian artery 44. For the incision 103 in the right subclavian artery 44, a suitable secondary incision site could be, for example, near the right femoral vein (not shown). A first guide-wire 114 is then directed percutaneously from the secondary incision site to the right subclavian artery 44 and through the introducer 104. The first guide-wire 114 is then directed into the distal end of the secondary delivery shaft 78. In some embodiments, the physician can direct the first guide-wire 114 through the entire length of the secondary delivery shaft 78, alternatively the first guide-wire 114 is advanced about 10 mm to about 20 mm into the secondary delivery shaft 78.

Figure 11:
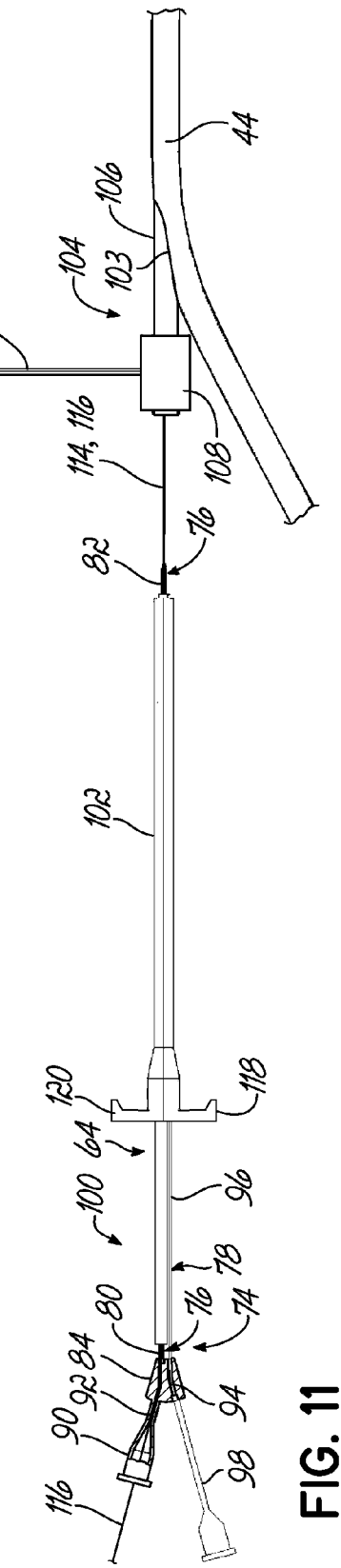

As shown in FIG. 11, a second guide-wire 116 is advanced through the primary lumen 86 (FIG. 4) of the multi-lumen tube 80 until it extends distally from the formed tip 82. The second guide-wire 116 is then advanced into the right subclavian artery 44 via the introducer 104.

With the guide-wires 114, 116 in position, the delivery system 100 with the delivery sheath 102 can be advanced, as a unit, into the introducer 104, as shown in FIG. 12, while the positions of the guide-wires 114, 116 and the introducer 104 are maintained. The delivery system 100 is advanced until the formed tip 82 is positioned as shown in FIG. 13, i.e., the formed tip 82 should be positioned distal to the delivery sheath 102 and within the right subclavian artery 44. In some embodiments, the formed tip 82 can include one or more radiopaque markers for in vivo visualization under a suitable viewing device during the positioning procedure. The physician then additionally, or alternatively, visualizes the positioning of the support structures 67, 68, 69 within the artery 44 (refer again to FIG. 1A). One such proper position can place the vascular conduit 62 just distal to the incision 103.

FIG. 14 illustrates the removal of the delivery sheath 102 to deploy the endovascular anastomotic connector 58. In embodiments where the delivery sheath 102 is constructed from a peel-away sheath design, the delivery sheath 102 is removed by pulling the ends 118, 120 of the delivery sheath 102 apart.

Once the delivery sheath 102 is sufficiently removed, the endovascular anastomotic connector 58 automatically deploys within the right subclavian artery 44. The proximal end 70 of the vascular conduit 62 is unfolded from around the supply conduit 64 and radially expanded against the inner wall of the right subclavian artery 44 by the support structure 67 (FIG. 1A). The supply conduit 64 can remain constrained by the sheath 106 of the introducer 104 during this manipulation.

As illustrated in FIG. 15, the first guide-wire 114 is retracted from its position within the secondary delivery shaft 78 and is advanced through the vascular conduit 62 and beyond the proximal end 70. The secondary delivery shaft 78 can then be removed.

The physician can then pull proximally on the multi-lumen delivery shaft 76 and the supply conduit 64 to reposition the vascular conduit 62 and bridge the incision 103 in the wall of the right subclavian artery 44. Repositioning is structurally supported by the multi-lumen delivery shaft 76. The introducer 104 and the multi-lumen delivery shaft 76 can then be retracted from the right subclavian artery 44 leaving the endovascular anastomotic connector 58, as shown in FIG. 16.

Figure 16:
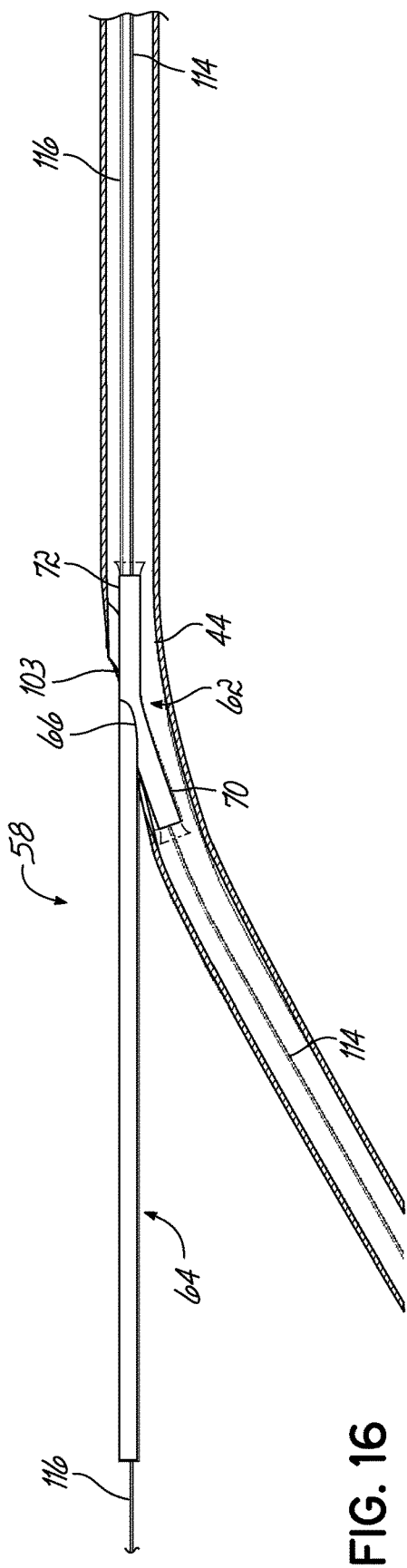

FIG. 16 further illustrates the proximal and distal ends 70, 72 of the vascular conduit 62 each including a flare (shown in phantom), which allows the vascular conduit 62 to accommodate a wider range of vessel sizes and to provide for a smooth transition between the vascular conduit 62 and the vessel.

Figure 17:
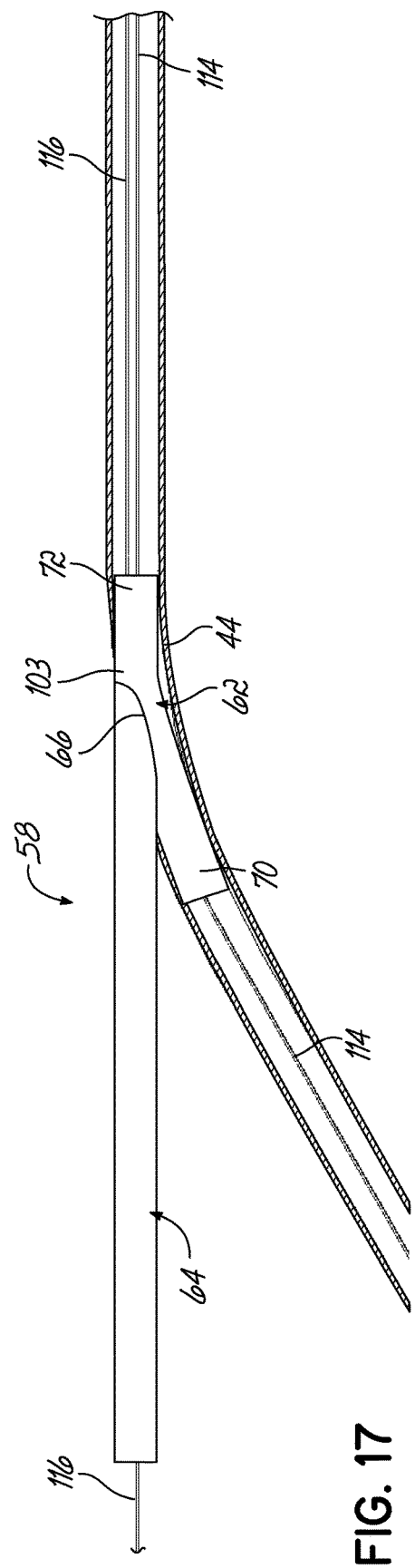
FIG. 17 is a side-elevational view, in partial cross section, of the deployed endovascular anastomotic connector in the peripheral artery.

Once the sheath 106 of the introducer 104 is removed, the support structure 69 (FIG. 1A) of the supply conduit 64 will cause the supply conduit 64 to automatically expand radially, as shown in FIG. 17.

Though not shown, the physician can ensure full radial expansion of the support structures 67, 68, 69 (FIG. 1A) by advancing a balloon dilation catheter to the endovascular anastomotic connector 58. The balloon dilation catheter can be advanced over the first or second guide-wires 114, 116 depending on which portion of the endovascular anastomotic connector 58 is being expanded. That is, to fully expand the vascular conduit 62, the balloon dilation catheter is advanced over the first guide-wire 114 and is positioned within the vascular conduit 62 at one of the support structures 67, 68 (FIG. 1A). The balloon dilation catheter is inflated and then deflated. The physician can then either remove or reposition the balloon dilation catheter at another support structure 68, 67 (FIG. 1A) within the vascular conduit 62.

To fully expand the bifurcation joint 66, the physician directs a balloon dilation catheter over the second guide-wire 116. Inflation of the balloon dilation catheter causes the bifurcation joint 66 to expand and seal the incision 103 in the wall of the right subclavian artery 44. In some embodiments, the physician can inflate and deflate the balloon dilation catheter multiple times, in the same or different positions, within the bifurcation joint 66 to ensure a complete expansion.

The balloon dilation catheter and guide-wires 114, 116 are then removed. The physician can then cap or clamp (not shown) the proximal end of the supply conduit 64 to prevent bleeding through its lumen. When attaching the auxiliary device to the supply conduit 64, the physician can deair the supply conduit 64 by back bleeding or inserting a needle through the cap to draw out the air.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A delivery system comprising:
   an anastomotic connector including:
   a vascular conduit having a proximal end, a distal end, and a lumen extending therebetween, wherein the vascular conduit is configured to reside within a vascular structure; and
   a supply conduit having a proximal end, a distal end, and a lumen extending therebetween, wherein the distal end of the supply conduit forms a bifurcation joint with the vascular conduit and the proximal end of the supply conduit is configured to extend from the vascular structure and couple to an auxiliary device; and
   a delivery subassembly, the delivery subassembly having an assembled position including:
   a multi-lumen hub having a first lumen and second lumen;
   a multi-lumen delivery shaft including a first lumen and a second lumen, the multi-lumen delivery shaft extending through the first lumen of the multi-lumen hub then through the lumen of the supply conduit, through the lumen of the distal end of the vascular conduit, and distally from the distal end of the vascular conduit; and
   a secondary delivery shaft extending through the second lumen of the multi-lumen hub then into the proximal end of the vascular conduit, through the lumen of the vascular conduit, and distally from the distal end of the vascular conduit, wherein a distal portion of the secondary delivery shaft extending distally from the distal end of the vasculature conduit and is received by a distal portion of the first lumen of the multi-lumen delivery shaft extending distally from the distal end of the vascular conduit.

2. The delivery system of claim 1, wherein the first lumen is slotted and configured to receive the secondary delivery shaft.

3. The delivery system of claim 1, wherein the multi-lumen delivery shaft includes the second lumen for receiving a guide-wire.

4. The delivery system of claim 1 further comprising:
   a delivery sheath configured to receive the delivery system and to move relative thereto.

5. The delivery system of claim 4, wherein the delivery sheath is constructed of a peel-away sheath design.

6. A delivery system comprising:
   a bifurcated stent having a body portion and a branch portion extending angularly from the body portion;
   a multi-lumen hub including a first lumen and second lumen; and
   an assembled position including:
   a multi-lumen delivery shaft extending through the first lumen of the multi-lumen hub, then through a lumen of the branch portion, through the lumen of a distal end of the body portion, and distally from the distal end of the body portion; and
   a secondary delivery shaft extending through the second lumen of the multi-lumen hub, then into a proximal end of the body portion, through the lumen of the body portion, and distally from the distal end of the body portion, wherein a distal portion of the secondary delivery shaft extending distally from the distal end of the body portion and is received by a distal portion of the first lumen of the multi-lumen delivery shaft extending distally from the distal end of the body portion.

7. The delivery system of claim 6 further comprising:
   a delivery sheath configured to receive the delivery system and to move relative thereto.

* * * * *